US005484431A

United States Patent [19]

Scharf et al.

[11] Patent Number: 5,484,431

[45] Date of Patent: Jan. 16, 1996

[54] SYSTEM FOR CREATING AT A SITE, REMOTE FROM A STERILE ENVIRONMENT, A PARENTERAL SOLUTION

[75] Inventors: Mike Scharf, McHenry; Mike Finley, Park City; Joe Veillon, McHenry; Jim Kipp; Tom Dudar, both of Palatine; Jim Owens, McHenry; Jim Ogle, Glenview, all of Ill.

[73] Assignee: The United States of America as represented by the Administrator of the National Aeronautics and Space Administration, Washington, D.C.

[21] Appl. No.: 647,109

[22] Filed: Jan. 29, 1991

[51] Int. Cl.$^6$ .................................................... A61M 5/00

[52] U.S. Cl. .......................... 604/403; 604/408; 604/416

[58] Field of Search .................................... 604/403–416, 604/247–253, 29, 85, 86; 141/325, 326, 327

[56] References Cited

U.S. PATENT DOCUMENTS

| | | | |
|---|---|---|---|
| 3,978,857 | 9/1976 | McPhee | 604/406 |
| 4,282,863 | 8/1981 | Beigler et al. | 604/410 |
| 4,396,382 | 8/1983 | Goldhaber | 604/28 |
| 4,458,733 | 7/1984 | Lyons | 604/410 X |
| 4,467,588 | 8/1984 | Carveth | 604/410 X |
| 4,504,265 | 3/1985 | Rudzena et al. | 604/86 |
| 4,664,650 | 5/1987 | Urquhart et al. | 604/85 |
| 4,874,344 | 10/1989 | Zdeb et al. | 604/56 |
| 4,906,103 | 3/1990 | Kao | 604/404 |
| 4,978,337 | 12/1990 | Theeuwes | 604/85 |
| 4,997,430 | 3/1991 | Van der Heiden et al. | 604/414 |

*Primary Examiner*—Sam Rimell
*Attorney, Agent, or Firm*—Mark J. Buonaiuto; Paul C. Flattery; Amy L. H. Rockwell

[57] ABSTRACT

The present invention relates to a container, system, and method for creating parenteral solutions at a site, remote from sterile environments. The system includes a flexible container that is empty except for a prepackaged amount of a solute that is housed in the interior of the container. The container includes at least one port and a sterilizing filter in communication with an interior of the port. The container is so constructed and arranged that a fluid flow path is created from the port through the filter and into the interior of the container. A sterile water source including means for establishing fluid flow from the sterile water source into the port is provided. Accordingly, sterile water can flow from the sterile water source through the filter into the container where it is mixed with the solute to create a parenteral solution that can then be infused into a patient. A method and container are also provided.

39 Claims, 1 Drawing Sheet

SYSTEM FOR CREATING AT A SITE, REMOTE FROM A STERILE ENVIRONMENT, A PARENTERAL SOLUTION

BACKGROUND OF THE INVENTION

The disclosed invention was funded, at least in part, by NASA.

The present invention relates generally to the creation of solutions for intravenous administration. More specifically, the present invention relates to the creation on site, remote from sterile environments, of parenteral (intravenous) solutions.

Of course, it is common practice to administer many solutions, medicaments, agents, and the like to a patient intravenously (parenterally). These solutions are typically housed in containers, that are constructed from flexible plastic or glass. Typically, these parenteral solutions are housed in containers having volume capacities of at least one liter, referred to as large volume parenteral containers.

Large volume parenteral containers typically include solutions such as saline, dextrose, or lactated Ringer's. Although these solutions can be administered to a patient alone, typically, an agent or medicament is added to the parenteral solution and the resultant product is then administered intravenously to the patient. Accordingly, the container includes a medication or additive port allowing an agent to be added to the container. Additionally, an access port is provided for accessing the container.

In use, the container is suspended and an IV line or other access means is utilized to access the container through the access port. Typically, the IV line includes a spike that is designed to pierce a membrane in the access port establishing fluid communication. A second end of the IV line is then directly inserted into the patient or coupled to a Y-site that provides fluid communication with the patient.

There are many situations wherein due to storage space and/or weight limitations, or other concerns, it is not possible, or practical, to maintain an adequate inventory of parenteral solutions that may be necessary. For example, space shuttles, or the envisioned space stations, have severe restrictions on the weight and volume of items that are stored or transported. Although it may be desirable to stock a number of intravenous solutions for use in an emergency, or for medical treatment, it is not possible due to weight and/or storage limitations to inventory a large volume of such solutions in many situations. Likewise, in other situations, such as in a combat zone, it may not be possible to transport the necessary parenteral solutions.

Still further, even within health care facilities, cost and storage limitations may limit the inventory of product that is purchased and stored. Therefore, it may be desirable to compound on the premises the necessary parenteral solutions.

Although it is known in certain applications to compound and/or reconstitute drugs prior to use, typically such reconstitution processes are performed in sterile conditions, for example, under a laminar flow hood. Such sterile conditions would not typically be present in certain situations wherein there exists severe weight and storage limitations, e.g., the aforementioned space station or combat zone. Likewise, current machinery for creating large volume parenteral products not only require sterile conditions, but also is quite bulky and heavy and not easily transportable.

Furthermore, typically reconstitution processes usually require either a prepackaged intravenous solution to assist in the reconstitution process, i.e., a bag of saline or dextrose, or can only be utilized to make small volumes of solutions. These processes therefore are not conducive to the creation of large volume parenteral containers.

SUMMARY OF THE INVENTION

The present invention relates to a container, system, and method for creating parenteral solutions at a site, remote from sterile environments. For example, it may be desirable in certain situations to create parenteral solutions immediately prior to use due to limited storage space and/or weight considerations.

The present invention provides such a system and method by providing a flexible container that is empty, except for a solute, and means for adding to the container sterile water so that the solute can be mixed with the sterile water to create a parenteral solution. Although the system and method can be used to create a parenteral solution that is then infused intravenously into a patient, the method for creating the parenteral solution can be performed in a nonsterile environment.

To this end, a system for creating at a site, remote from a sterile environment, a parenteral solution in a large volume parenteral container is provided. The system includes a flexible container that is empty except for a prepackaged amount of a solute that is housed in the interior of the container. The container includes at least one port and a sterilizing filter in communication with an interior of the port. The container is so constructed and arranged that a fluid flow path is created from the port through the filter and into the interior of the container. A sterile water source including means for establishing fluid flow from the sterile water source into the port is provided. Accordingly, sterile water can flow from the sterile water source through the filter into the container where it is mixed with the solute to create a parenteral solution that can then be infused into a patient.

In an embodiment, a system for creating at a site, remote from a sterile environment, a parenteral solution in a large volume parenteral container is provided. The system includes a flexible container including an interior that is empty except for a prepackaged amount of a solute. The interior of the container includes means for creating turbulence and a flow path within the interior. The container includes a sterile filter and a first port so constructed and arranged that fluid enters the first port and flows through the filter into the interior of the container. A source of sterile water including means for establishing fluid communication between the source of sterile water and the port is provided. Accordingly, a solute can be positioned within the container and sterile water can be injected, through the port and filter, into the container and due to the means for establishing turbulence and a fluid flow path, a mixing of the solute and water is achieved allowing a resultant parenteral solution to be created.

In an embodiment of the present invention, the solute is a powder.

In an embodiment of the present invention, the solute is a liquid concentrate.

In an embodiment of the present invention, the solute includes a component chosen from the group consisting of: dextrose; sodium chloride; and lactated Ringer's.

In an embodiment, a container is provided for reconstituting a parenteral solution. The container includes a flexible body defining an interior including means for creating turbulence and at least one fluid flow path within the interior of the container. A sterile filter is provided that is coupled to the container and is in fluid communication with a first opening that provides a fluid flow path between the filter and an interior of the container. A port in fluid communication with an end of the sterile filter is also provided. The container is so constructed and arranged that a fluid flow path is provided from the port, through the filter, through the first opening and into the interior of the container.

The present invention also provides a method for creating parenteral solutions at a site remote from a sterile environment. The method comprises the steps of: providing a flexible container that is empty except for a prepackaged solute; providing the flexible container with a port and sterilizing filter assembly; coupling the port to a sterile water source; allowing sterile water from the sterile water source to flow through the port and sterilizing filter into an interior of the container; and allowing the sterile water to mix with the solute to create a parenteral solution.

In an embodiment of the method, the solute is a powder.

In an embodiment of the method, the solute is a liquid concentrate.

In an embodiment of the method, the solute includes a component chosen from the group consisting of: dextrose; sodium chloride; and lactated Ringer's.

In an embodiment of the method, an agent is added to the resultant parenteral solution.

In an embodiment of the method, the parenteral solution is administered intravenously to a patient.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a container, system, and method for formulating a predetermined amount of a sterile solution by combining a premeasured, prepackaged amount of solute, that can be present either in a powder or liquid concentrate form, with a predetermined amount of sterile water. The solute is contained in a large volume parenteral container that is flexible so as to have a limited size and weight prior to formulation of the parenteral solution. Because the sterile water source can be any device that creates sterile water, from a nonsterile water source, this greatly reduces the weight and volume of the large volume parenteral containers that can be created as compared to typical prepackaged large volume parenteral containers.

The present invention provides many advantages including that parenteral solutions can be created in a nonsterile environment. This allows the components necessary to create a variety of parenteral solutions to be easily transported and then used to create solutions as necessary. The advantages of such a system are limitless and include use in situations where weight and storage limitations present problems in maintaining sufficient inventories, e.g., space stations and combat zones.

Figure 1:
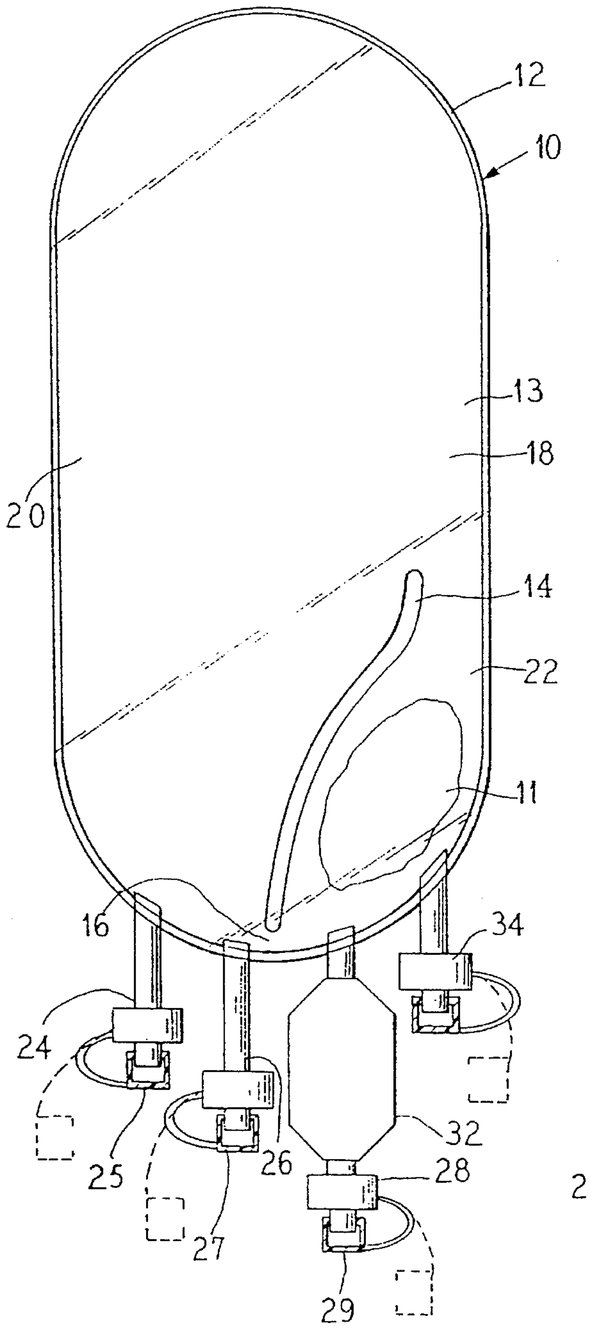
FIG. 1 illustrates a cross-sectional perspective view of a container of the present invention for creating at a site, remote from a sterile environment, a parenteral solution.

Referring now to FIG. 1, the system of the present invention includes a flexible container 10. The container 10 includes a body 12 constructed from a flexible plastic material such as polyvinyl chloride, ethylene vinyl acetate, other polyolefins, or combinations thereof. Pursuant to the present invention, the container 10 is empty during storage except for a solute 11 that is located within the interior 13 of the container.

The solute can be any composition that can create parenteral solutions. As used herein, a solute refers to a composition that when combined with water, or other fluid, creates a parenteral solution. For example, the solute can be sodium chloride, dextrose, or lactated Ringer's. The solute can be in a liquid concentrate or powder form except in the case of lactated Ringer's wherein the solute is preferably a liquid concentrate. Presently, due to sterilization techniques, the liquid concentrate form of the solute may be preferable. As discussed in more detail hereinafter, pursuant to the present invention, the solute is mixed with sterile water to create a parenteral solution.

By way of example, the following solutes can be used to create one liter of a resultant parenteral solution when combined with sterile water. Liquid concentrate solutes include: 9 g/50 mL sodium chloride; 71.4 ml of 70% dextrose; 40 mL of lactated Ringer's concentrate B (5.94 gm sodium chloride, 0.297 mg potassium chloride, 0.198 mg calcium chloride dihydrate, 3.07 gm sodium lactate); and 50 mL of lactated Ringer's concentrate C (5.94 gm sodium chloride, 0.297 mg potassium chloride, 0.198 mg calcium chloride dihydrate, 3.07 gm sodium lactate). Powder: 9 grams sodium chloride, for example, available from International Salt; 45.5 grams dextrose anhydrous, for example, available from Corn Products; and 50 grams dextrose monohydrate, for example, available from Mallinkrodt.

When mixed with approximately one liter of water, the solutes will create: saline, either normal or half normal, i.e., 0.45% saline; dextrose, e.g., 5% dextrose; and lactated Ringer's. These resultant solutions can then be intravenously administered to a patient.

Located within the container 10, in the preferred embodiment illustrated, is an internal seal 14. The internal seal 14 can be created in a number of ways, for example, by placing a plastic member between the two faces that define the body 12 of the container 10 or sealing the two faces together at a predetermined area. The seal 14 defines two areas 20 and 22 within the interior 13 of the container 10. Additionally, the seal 14 defines two gaps 16 and 18 within the interior 13 of the container 10 that allow fluid flow between the two areas 20 and 22.

Preferably, in use, the solute 11 is located in area 22. As discussed in more detail hereinafter, the seal 14 creates a flow path within the interior 13 of the container 10. The seal 14 also functions to create turbulence when fluid flows into the container 10 ensuring an adequate mixing of the solute and sterile water that is used to create a parenteral solution within the container 10.

As illustrated, preferably, the container 10 includes a plurality of ports. Of course, the container 10 can include any number of ports and although four ports are illustrated, a greater or lesser number of ports can be provided.

In the illustrated embodiment, the container includes a first port 24 that functions as a medication port. The first port 24 allows one to inject an agent or medicament into the container. It is standard practice to inject a medicament or agent into a parenteral container including a parenteral solution so that the resultant solution and agent can then be infused into a patient.

The first port 24 provides a means for providing access to the interior 13 of the parenteral container 10 so that an agent or medicament can be added. The parenteral container 10 can be accessed through the first port 24 utilizing a variety of methods depending on the environments wherein the resultant product will be used. For example, it is known, in typical parenteral containers to use a syringe having a pointed cannula that is inserted through a resealable, pierceable membrane that is located within an interior of the port. Likewise, access to the container can be through a needleless syringe and preslit injection site. Such a preslit membrane and cannula is disclosed in U.S. patent application Ser. No. 07/147,414, "Preslit Injection Site and Associated Cannula" abandoned in favor of U.S. patent application Ser. No. 07/539,278, the disclosure of which is incorporated herein by reference. The needleless syringe includes a cannula having a blunt end that is received within a preslit injection site.

In the embodiment of the invention illustrated, the first port 24 includes, in an interior thereof, a one way valve that allows an agent to be injected into the interior of the container 10, but prevents fluid flow out of the container. An example of such a valve is the one way check valve produced by Burron Medical Corporation. The advantage of such a system that does not require a pointed cannula is with respect to trash disposable and accidental "sticks" that can occur with a pointed cannula. If desired, to allow fluid flow into and out of the container, a bidirectional valve, such as available from Burron Medical Corporation, can be used.

The illustrated embodiment also includes a sterile port protector 25 or cap. The port protector 25 ensures the sterility of the interior of the first port 24 until it is desired to access the container 10 through the first port 24. Preferably, to limit trash generation, the port protector 25 is tethered to the port 24.

A second port 26 is provided that functions to allow one to access the fluid contained within the parenteral container 10. To this end, the second port 26 is designed to receive a spike or other means for accessing the container. Typically, such a spike is a part of an administration set and can be used to administer intravenously the parenteral solution contained within the container 10 to a patient. Preferably, a bidirectional valve is used in the second port 26. Likewise, a port protector 27 is provided that is tethered to the second port 26.

A third port 28 is provided including a tethered port protector 29. The third port 28 is designed to allow a fluid such as sterile water to flow into the interior 13 of the container 10. To this end, the third port 28 includes means for allowing, as discussed in more detail hereinafter and illustrated in FIG. 2, a sterile water source 30 to be coupled to the third port 28 and provide fluid flow from the sterile water source through the third port 28. The third port 28 terminates at and provides fluid communication with a sterilizing filter 32. Of course, the third port 28 and the filter 32 can be integral and the same unit. Preferably, the third port includes a bidirectional valve.

The sterilizing filter 32 is designed to sterilize fluid that flows from the third port 28 through the filter and then into the interior 13 of the container 10. For example, a 0.22 micron sterilizing filter 32 can be utilized. Thus, a fluid flow path is provided from the third port 28 through the sterilizing filter 32 and into an interior 13 of the container 10.

In an embodiment, the sterilizing filter 32 is removably secured to the container 10. To this end, a luer connection or the like can be used to removably secure the filter to the container. This allows the sterile filter 32 to be removed after the parenteral solution has been created in the container. To accomplish this, a bidirectional valve can be located between the container and the filter so that when the filter is removed, fluid does not flow out of the container.

The advantage of this structure, in part, is with respect to long term storage of the resultant parenteral solution containing containers. If stored for a long period of time, there is a potential for growth through the filter that could potentially contaminate the solution in the containers.

Although a fourth port 34 is provided in the embodiment illustrated, the fourth port 34 is a redundant, extra port, and of course can be deleted if desired. The fourth port 34 provides means for allowing a second agent to be introduced into the container or to provide other accessing requirements and/or needs.

Figure 2:
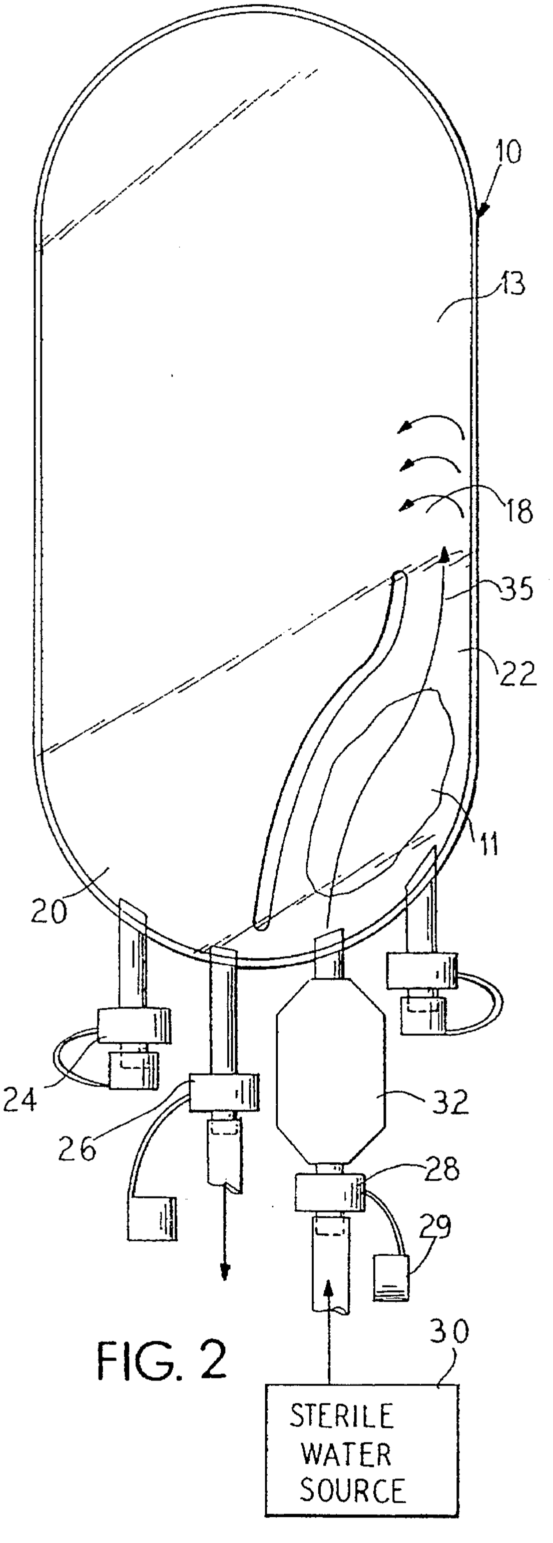
FIG. 2 illustrates a cross-sectional perspective view of a parenteral solution being created in the container of FIG. 1 pursuant to the present invention.

As previously stated, the system of the present invention also includes a sterile water source 30 that, as illustrated in FIG. 2, is designed to couple with the third port 28 and allows sterile water to be pumped through the third port 28 and the filter 32 into the interior 13 of the container 10. When sterile water is so pumped it is passed through the sterilizing filter 32.

Due to the construction of the interior 13 of the container 10, and specifically, the seal 14, turbulence is created and a flow path 35 established through the area 22 up through the gap 18. Because the solute 12 is located in area 22, this causes a mixing of the sterile water and the solute creating the desired parenteral product within the interior 13 of the flexible container 10.

The sterile water source 30 can be any sterile water source that creates sterile water that is fed into the device. For example, the sterile water source 30 can be the Sterile Water for Injection System (SWIS), developed by the Sterimatics Division of Millipore Corporation for NASA. Such a system includes a particulate filter, activated charcoal filter, cation bed, anion bed and microbial filter.

The system of the present invention allows parenteral solutions, such as dextrose solutions, saline, and lactated Ringer's to be created that are ready to use. Even in the case of dextrose powders, it has been found that the dissolution rates of the powder are such that containers of parenteral solution can be created on an expedited basis. For example, assuming that the sterile water source 30 can produce no more than six liters of sterile water per hour, the fill time of a one liter parenteral container would be ten minutes. Ten minutes is sufficient time to dissolve the necessary dextrose powder allowing a 5% dextrose solution to be created that can then be administered intravenously.

The sterile water source 30 can include a metering device (not shown) to ensure that only one liter of water is injected into the container, if a one liter solution is to be created. Of course, the metering device can also, if desired, be coupled to the container 10. Additionally, a clamshell or other structure (not shown) can be used that circumscribes the flexible container 10. The clamshell can be designed to only allow the container to accept a predetermined amount of fluid.

By way of example and not limitation, projected weights and volume for the embodiments of the invention are as follows:

| Embodiment | Approximate Volume (Solute) mL | Approximate Weight (Solute) grams | Approximate Volume (Package) mL | Approximate Weight (Filled Package) grams |
|---|---|---|---|---|
| | Powder in 1-liter bag | | | |
| Lactated Ringer's | — | — | — | — |
| Normal Saline | 6.47 | 9.00 | 229.67 | 65.00 |
| Half-Normal Saline | 3.24 | 4.50 | 229.67 | 69.50 |
| 5% Dextrose | 45.00 | 45.50 | 229.67 | 115.00 |
| | Concentrate in 1-liter bag | | | |
| Lactated Ringer's | 40.00 | 47.7 | 229.57 | 120.00 |
| Normal Saline | 50.00 | 58.10 | 229.67 | 120.33 |
| Half-Normal Saline | 25.00 | 29.05 | 229.67 | 91.28 |
| 5% Dextrose | 71.40 | 91.60 | 229.67 | 157.67 |

The above volumes and weights allow a number of possible parenteral solutions to be created as needed with a limited space and weight requirement.

For example, based on the above, the system of the present invention provides the ability to make 120 one liter parenteral solutions, 30 each of 5% dextrose, normal saline, half-normal saline, and lactated Ringer's using only the following volume and weight of components, exclusive of the sterile water source:

| | | | |
|---|---|---|---|
| | Weight Calculations 1-Liter Bag - Powder | | |
| 5% Dextrxose | 115.0 Grams/Unit | 3450 Grams | 30.38% |
| Normal Saline | 74.0 Grams/Unit | 2220 Grams | 19.55% |
| Half-Normal Saline | 69.5 Grams/Unit | 2085 Grams | 18.36% |
| Lactated Ringer's | 120.0 Grams/Unit | 3600 Grams | 31.70% |
| | Total Weight | 11355 Grams | 100.00% |
| | Volume Calculations 1-Liter Bag - Powder | | |
| 5% Dextrose | 229.7 mL | 6890.10 mL | 25.00% |
| Norml Saline | 229.7 mL | 6890.10 mL | 25.00% |
| Half-Normal Saline | 229.7 mL | 6890.10 mL | 25.00% |
| lactated Ringer's | 229.7 mL | 6890.10 mL | 25.00% |
| | Total Volume | 27560.40 mL | 100.00% |
| | Alternatively, if a liquid cmcentrate is used: Weight Calculations 1-Liter Bag - Concentrate | | |
| 5% Dextrose | 157.7 Grams/Unit | 4791 Grams | 32.22% |
| Norml Saline | 120.3 Grams/Unit | 3609 Grams | 24.59% |
| Half-Normal Saline | 91.3 Grams/Unit | 2739 Grams | 18.66% |
| Lactated Ringer's | 120.0 Grams/Unit | 3600 Grams | 24.52% |
| | Total Weight | 58720 Grams | 100.00% |
| | Volume Calculations 1-Liter Bag - Concentrate | | |
| 5% Dextrose | 229.7 mL | 6890.10 mL | 25.00% |
| Normal Saline | 229.7 mL | 6890.10 mL | 25.00% |
| Half-Normal Saline | 229.7 mL | 6890.10 mL | 25.00% |
| Lactated Ringer's | 229.7 mL | 6890.10 mL | 25.00% |
| | Total Volume | 27560.40 mL | 100.00% |

By way of further example, one liter parenteral solutions can be created each of 120 dextrose, normal saline, half-normal saline, and lactated Ringer's using only the following volume and weight of components:

Weight Calculations

-continued

| | | | |
|---|---|---|---|
| | 1-Liter Bag - Powder | | |
| 5% Dextrose | 115.0 Grams/Unit | 13800 Grams | 30.38% |
| Normal Saline | 74.0 Grams/Unit | 8880 Grams | 19.55% |
| Half-Normal Saline | 69.5 Grams/Unit | 8340 Grams | 18.36% |
| Lactated Ringer's | 120.0 Grams/Unit | 14400 Grams | 31.70% |
| | Total Weight | 45420 Gram | 100.00% |
| | Volume Calculations 1-Liter Bag - Powder | | |
| 5% Dextrose | 229.7 mL | 27560.40 mL | 25.00% |
| Normal Saline | 229.7 mL | 27560.40 mL | 25.00% |
| Half-Normal Saline | 229.7 mL | 27560.40 mL | 25.00% |
| Lactated Ringer's | 229.7 mL | 27560.40 mL | 25.00% |
| | Total Volume | 110241.60 mL | 100.00% |
| | Alternatively, for a liquid concentrate solute: Weight Calculations 1-Liter Bag - Concentrate | | |
| 5% Dextrose | 157.7 Grams/Unit | 18920 Grams | 32.22% |
| Normal Saline | 120.3 Grams/Unit | 14440 Grams | 24.59% |
| Half-Normal Saline | 91.3 Grams/Unit | 10960 Grams | 18.66% |
| Lactated Ringer's | 120.0 Grams/Unit | 14400 Grams | 24.52% |
| | Total Weight | 58720 Grams | 100.00% |
| | Volume Calculations 1-Liter Bag - Concentrate | | |
| 5% Dextrose | 229.7 mL | 27560.40 mL | 25.00% |
| Normal Saline | 229.7 mL | 27560.40 mL | 25.00% |
| Half-Normal Saline | 229.7 mL | 27560.40 mL | 25.00% |
| Lactated Ringer's | 229.7 mL | 27560.40 mL | 25.00% |
| | Total Volume | 110241.60 mL | 100.00% |

Examples of methods of using the present invention are as follows:

The flexible bag is preferably packaged in a foil pouch from which it is removed. The port protector from the inlet or third port that is coupled to the filter is removed. A sterile water source is connected to the container by coupling the outlet of the source to the inlet port on filter. The source begins to create sterile water and the flow of water is initiated from the water source into the interior of the container. Creating the sterile water and filling of the container will take approximately 10 minutes.

The bag is allowed to fill. The bag is inspected at approximately 3 minute intervals for the presence of undissolved powder. The bag is kneaded as required to dissolve the powder. No visible powder should remain after filling. The sterile water source is then disconnected from the container. The parenteral solution has now been created.

If it is desired to add a medicament to the solution, in an embodiment, this can be accomplished as follows. A prefilled syringe containing prescribed medication can be used. Again, any means for injecting an additive into a parenteral container can be used. A port protector is removed from the tip of prefilled syringe as well as the port protector from the medication site. The syringe is connected to the medication port, or first port. The medication is injected into the container.

The port protector is removed from outlet or second port of the container. The outlet port of the container is then connected to the inlet of an administration set. The set is purged of air and then is connected to the patient; the flow of the IV solution to the patient can then be accomplished.

In an embodiment of the method of the present invention wherein a concentrate is used, the method is substantially the same as set forth for the powder. The only difference is with respect to creating the solution which is as follows.

Remove the bag from foil pouch. Remove the port protector from inlet port on filter. Connect the outlet of the sterile water source to inlet port on filter. Initiate flow of water through the sterile water source. Filling will take approximately 10 minutes. Allow bag to fill.

Initial sterilization of the system can be accomplished for liquid concentrate embodiments using conventional techniques. To this end, the container 10 and solute can be terminally sterilized. If powders are used, sterilization is more difficult but it may be possible to terminally sterilize the container and powder through gamma irradiation. However, it is possible to manufacture the powder under sterile conditions and then fill the container with powder under sterile conditions.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A system for creating at a site, remote from a sterile environment, a parenteral solution in a large volume parenteral container comprising:

a flexible container having an interior that is empty prior to adding a fluid except for a prepackaged amount of a solute that is housed in the interior of the container, the container including at least one port, and a sterilizing filter in fluid communication with the interior and the port, the container being so constructed and arranged that the fluid flows from the port, through the filter and into the interior of the container; and a source of sterile water including means for establishing fluid flow from the source of sterile water into the port.

2. The system of claim 1 wherein the solute is a powder.

3. The system of claim 1 wherein the solute is a liquid concentrate.

4. The system of claim 1 wherein the solute includes a component chosen from the group consisting of: dextrose; sodium chloride; and lactated Ringer's.

5. The system of claim 1 wherein the container includes means for defining at least two areas in the interior of the container that are in fluid communication.

6. The system of claim 1 wherein the interior of the container includes a sealed portion that allows fluid flow across a bottom portion and a top portion of the seal.

7. The system of claim 1 wherein the container includes at least one medication port and an administration port.

8. The system of claim 1 wherein the parenteral solution created is chosen from the group consisting of: saline; dextrose; and lactated Ringer's.

9. The system of claim 1 wherein the filter and the port are integral.

10. The system of claim 1 wherein the filter is removably secured to the container.

11. A system for creating at a site, remote from a sterile environment, a parenteral solution in a large volume parenteral container comprising:

a flexible container including an interior that is empty prior to adding a fluid except for a prepackaged amount of a solute and a means for creating turbulence wherein the means for creating turbulence forms a flow path within the interior, the container in fluid communication with a sterilizing filter and a first port so constructed and arranged that the fluid enters the port and flows through the filter and into the interior of the container; and a source of sterile water including means for establishing fluid communication between the source of sterile water and the port.

12. The system of claim 11 wherein the solute is a powder.

13. The system of claim 11 wherein the solute is a liquid concentrate.

14. The system of claim 11 wherein the solute includes a component chosen from the group consisting of: dextrose; sodium chloride; and lactated Ringer's.

15. The system of claim 11 wherein the parenteral solution created is chosen from the group consisting of: saline; dextrose; and lactated Ringer's.

16. The system of claim 11 wherein the means for creating turbulence and the flow path is a seal located within the interior of the container.

17. The system of claim 11 wherein the container includes at least one medication port and an administration port.

18. The system of claim 11 wherein the first port includes a one way valve.

19. The system of claim 11 wherein the first port includes a bidirectional valve.

20. The system of claim 11 wherein the filter is removably coupled to the container.

21. A container for reconstituting a parenteral solution comprising:

a flexible body having an interior that is empty prior to adding a fluid except for a prepackaged amount of a solute and a means for creating turbulence wherein the means for creating turbulence forms at least one fluid flow path within the interior, a sterilizing filter coupled to the container and in fluid communication with a first opening in the container allowing the fluid to flow from the filter into the interior of the container, and a port in fluid communication with an end of the sterilizing filter, the container being so constructed and arranged that fluid flow is from the port, through the filter, and into the interior of the container.

22. The container of claim 21 wherein the solute is a powder.

23. The container of claim 21 wherein the solute is a liquid concentrate.

24. The container of claim 21 wherein the solute includes a component chosen from the group consisting of: dextrose; sodium chloride; and lactated Ringer's.

25. The system of claim 21 wherein the means for creating turbulence and a flow path is a seal located within the interior.

26. The container of claim 21 wherein the parenteral solution created is chosen from the group consisting of: saline; dextrose; and lactated Ringer's.

27. The container of claim 21 wherein the container includes at least one medication port and an administration port.

28. The container of claim 21 wherein the port includes a one-way valve.

29. The container of claim 21 wherein the port 10 includes a bidirectional valve.

30. The container of claim 21 wherein the filter is removably coupled to the container.

31. The container of claim 21 wherein the means for creating turbulence and at least one fluid flow path defines two areas within the interior of the container, the solute being located in a first of the two areas.

32. A method for creating parenteral solutions in large volume containers comprising the steps of:

providing a flexible container having an interior that is empty prior to adding a fluid except for a prepackaged solute;

providing the flexible container with a port outside the container and a sterilizing filter assembly in fluid communication with the interior of the container and the port;

coupling the port to a sterile water source;

allowing sterile water from the water source to flow through the filter into the interior of the container; and allowing the water to mix with the solute to create a parenteral solution.

33. The method of claim 32 including the step of creating sterile water that is fed into the container from a nonsterile water source approximately contemporaneously with the flow of the water into the container.

34. The method of claim 32 including the step of adding to the resultant parenteral solution a medicament.

35. The method of claim 32 wherein the solute is a powder.

36. The method of claim 32 wherein the solute is a liquid concentrate.

37. The method of claim 32 wherein the solute includes a component chosen from the group consisting of: dextrose; sodium chloride; and lactated Ringer's.

38. The method of claim 32 wherein the parenteral solution created is chosen from the group consisting of: saline; dextrose; and lactated Ringer's.

39. The method of claim 32 including the step of removing the filter from the container after creating the parenteral solution.

* * * * *